(12) United States Patent
Hakozaki et al.

(10) Patent No.: US 11,110,049 B2
(45) Date of Patent: *Sep. 7, 2021

(54) COMPOSITION AND METHOD FOR IMPROVING THE APPEARANCE OF SKIN

(71) Applicant: The Procter & Gamble Company, Cincinnati, OH (US)

(72) Inventors: Tomohiro Hakozaki, Cincinnati, OH (US); John Erich Oblong, Loveland, OH (US); Bin Fang Deyer, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/860,837

(22) Filed: Apr. 28, 2020

(65) Prior Publication Data

US 2020/0253851 A1 Aug. 13, 2020

Related U.S. Application Data

(62) Division of application No. 16/015,502, filed on Jun. 22, 2018, now Pat. No. 10,660,838.

(60) Provisional application No. 62/523,840, filed on Jun. 23, 2017.

(51) Int. Cl.
*A61K 8/60* (2006.01)
*A61K 8/34* (2006.01)
*A61K 8/67* (2006.01)
*A61Q 19/00* (2006.01)
*A61Q 19/08* (2006.01)

(52) U.S. Cl.
CPC ............... *A61K 8/60* (2013.01); *A61K 8/342* (2013.01); *A61K 8/675* (2013.01); *A61Q 19/00* (2013.01); *A61Q 19/08* (2013.01); *A61K 2800/48* (2013.01)

(58) Field of Classification Search
CPC .......... A61K 8/60; A61K 8/342; A61K 8/675; A61K 2800/48; A61Q 19/08; A61Q 19/00
USPC .......................................................... 424/59
See application file for complete search history.

(56) References Cited

U.S. PATENT DOCUMENTS

| | | |
|---|---|---|
| 3,755,560 A | 8/1973 | Dickert et al. |
| 3,856,941 A | 12/1974 | Turner |
| 3,859,436 A | 1/1975 | Jacobi |
| 3,867,549 A | 2/1975 | Costello |
| 3,892,853 A | 7/1975 | Cobble |
| 4,007,266 A | 2/1977 | Choay |
| 4,178,372 A | 12/1979 | Coats |
| 4,406,884 A | 9/1983 | Fawzi |
| 4,421,769 A | 12/1983 | Dixon |
| 4,481,187 A | 11/1984 | Kondo |
| 4,485,091 A | 11/1984 | Fitton |
| 4,792,443 A | 12/1988 | Filomeno |
| 4,879,107 A | 11/1989 | Vanlerberghe |
| 4,923,977 A | 5/1990 | Lang |
| 5,053,230 A | 10/1991 | Gazzani |
| 5,140,043 A | 8/1992 | Darr |
| 5,229,104 A | 7/1993 | Sottery |
| 5,302,376 A | 4/1994 | Forestier |
| 5,346,694 A | 9/1994 | Juneja |
| 5,419,896 A | 5/1995 | Bimczok |
| 5,429,815 A | 7/1995 | Faryniarz |
| 5,496,538 A | 3/1996 | Zimmerman |
| 5,520,918 A | 5/1996 | Smith |
| 5,549,886 A | 8/1996 | Grollier |
| 5,549,888 A | 8/1996 | Venkateswaran |
| 5,567,427 A | 10/1996 | Papadakis |
| 5,607,921 A | 3/1997 | Bernard |
| 5,616,332 A | 4/1997 | Herstein |
| 5,629,004 A | 5/1997 | Candau |
| 5,654,341 A | 8/1997 | Struewing |
| 5,707,635 A | 1/1998 | Deckner |
| 5,718,906 A | 2/1998 | Martin |
| 5,718,908 A | 2/1998 | Fanelli |
| 5,736,128 A | 4/1998 | Chaudhuri |
| 5,759,558 A | 6/1998 | Epstein |
| 5,824,666 A | 10/1998 | Deckner |
| 5,833,998 A | 11/1998 | Biedermann |
| 5,871,764 A | 2/1999 | Diaz |
| 5,872,112 A | 2/1999 | Blank |
| 5,876,736 A | 3/1999 | Cohen |
| 5,939,082 A | 8/1999 | Oblong |
| 5,961,999 A | 10/1999 | Bimczok |
| 5,968,528 A | 10/1999 | Deckner et al. |
| 5,972,359 A | 10/1999 | Sine |
| 5,989,536 A | 11/1999 | Deckner |
| 5,993,832 A | 11/1999 | Lorant |
| 6,001,379 A | 12/1999 | Griat |
| 6,042,813 A | 3/2000 | Fowler |
| 6,045,779 A | 4/2000 | Mueller |
| 6,099,825 A | 8/2000 | Mcshane |
| 6,153,176 A | 11/2000 | Kaleta |
| 6,174,533 B1 | 1/2001 | Sanogueira, Jr. |
| 6,217,887 B1 | 4/2001 | Beerse |
| 6,218,347 B1 | 4/2001 | Rau |
| 6,238,678 B1 | 5/2001 | Oblong et al. |

FOREIGN PATENT DOCUMENTS

| | | |
|---|---|---|
| AU | 2005293830 B2 | 10/2010 |
| AU | 2016206278 A1 | 2/2017 |

(Continued)

OTHER PUBLICATIONS

Lambers et al. Natural skin surface pH is on average below 5, which is beneficial for its resident flora. International Journal of Cosmetic Science, 2006, 28, 359-370. (Year: 2006).*

(Continued)

*Primary Examiner* — Yih-Horng Shiao
(74) *Attorney, Agent, or Firm* — John G. Powell

(57) ABSTRACT

Low pH cosmetic compositions and methods for improving the appearance of skin. The low pH cosmetic compositions herein include a saccharide and, optionally, one or more additional skin care actives to improve the appearance of skin. The lower pH reduces or even eliminates some of the skin health and appearance drawbacks associated with saccharide induced glycation.

16 Claims, 2 Drawing Sheets

(56) References Cited

U.S. PATENT DOCUMENTS

| | | |
|---|---|---|
| 6,261,541 B1 | 7/2001 | Karpov |
| 6,281,203 B1 | 8/2001 | Touzan |
| 6,287,582 B1 | 9/2001 | Gott |
| 6,287,583 B1 | 9/2001 | Warren |
| (Continued) | | |
| 6,299,885 B1 | 10/2001 | Yamasaki |
| H0002013 H | 2/2002 | Boyd et al. |
| 6,387,918 B1 | 5/2002 | Yamanaka |
| 6,410,039 B1 | 6/2002 | Walker |
| 6,416,768 B1 | 7/2002 | Ravaux |
| 6,419,907 B1 | 7/2002 | Hocquaux |
| 6,432,415 B1 | 8/2002 | Osborne |
| 6,440,432 B1 | 8/2002 | Mukherjee |
| 6,440,437 B1 | 8/2002 | Krzysik |
| 6,461,622 B2 | 10/2002 | Liu |
| 6,468,549 B1 | 10/2002 | Dupuis |
| 6,492,326 B1 | 12/2002 | Robinson |
| 6,524,598 B2 | 2/2003 | Sunkel |
| 6,585,984 B1 | 7/2003 | Scott |
| 6,632,444 B1 | 10/2003 | Zhou |
| 6,638,519 B1 | 10/2003 | Lorant |
| 6,682,750 B2 | 1/2004 | Loeffler |
| 6,696,049 B2 | 2/2004 | Vatter |
| 6,706,259 B1 | 3/2004 | Gardner |
| 6,759,051 B2 | 7/2004 | Saint-leger |
| 6,831,107 B2 | 12/2004 | Dederen |
| 6,903,210 B2 | 6/2005 | Behrends |
| 6,906,106 B2 | 6/2005 | Chevalier |
| 6,932,976 B2 | 8/2005 | Brooks |
| 6,979,452 B2 | 12/2005 | Zhou |
| 6,986,895 B2 | 1/2006 | Suares |
| 7,018,660 B2 | 3/2006 | Murad |
| 7,176,191 B2 | 2/2007 | Dale |
| 7,179,771 B1 | 2/2007 | Charlton |
| 7,291,351 B2 | 11/2007 | Azik |
| 7,300,678 B2 | 11/2007 | Paufique |
| 7,332,152 B2 | 2/2008 | Sanzgiri |
| 7,378,083 B2 | 5/2008 | Stephens |
| 7,416,719 B2 | 8/2008 | Huerta |
| 7,455,849 B2 | 11/2008 | Utschig |
| 7,741,366 B2 | 6/2010 | Mackles |
| 7,799,356 B2 | 9/2010 | Raschke |
| 7,815,900 B1 | 10/2010 | Cannell et al. |
| 7,829,107 B2 | 11/2010 | Popp |
| 8,063,097 B2 | 11/2011 | Robinson |
| 8,106,184 B2 | 1/2012 | Sauve |
| 8,197,807 B2 | 6/2012 | Brenner |
| 8,293,279 B2 | 10/2012 | Schiffer |
| 8,293,784 B2 | 10/2012 | Rudolph |
| 8,329,758 B2 | 12/2012 | Ali |
| 8,343,902 B2 | 1/2013 | Walters |
| 8,383,086 B2 | 2/2013 | Brenner |
| 8,435,950 B2 | 5/2013 | Dal Farra |
| 8,475,851 B2 | 7/2013 | Herrmann |
| 8,491,464 B2 | 7/2013 | Yokoi |
| 8,529,920 B2 | 9/2013 | Liu |
| 8,529,979 B2 | 9/2013 | Abril |
| 8,546,364 B2 | 10/2013 | Patel |
| 8,652,447 B2 | 2/2014 | Maesen |
| 8,828,410 B2 | 9/2014 | Sakuta |
| 8,883,215 B2 | 11/2014 | Beck |
| 8,895,034 B2 | 11/2014 | Bennett |
| 8,895,513 B2 | 11/2014 | Trudsoe |
| 8,911,774 B2 | 12/2014 | Giampapa |
| 8,933,217 B2 | 1/2015 | Rinsch |
| 8,968,755 B2 | 3/2015 | Schlessinger |
| 8,999,923 B2 | 4/2015 | Cao |
| 9,068,148 B2 | 6/2015 | Tamareselvy |
| 9,084,734 B2 | 7/2015 | Collier |
| 9,186,304 B2 | 11/2015 | Claas |
| 9,271,912 B2 | 3/2016 | Fernandez Prieto |
| 9,283,163 B2 | 3/2016 | Santhanam |
| 9,339,447 B2 | 5/2016 | Souzy |
| 9,364,414 B2 | 6/2016 | Domloge |
| 9,364,690 B2 | 6/2016 | Lorant |
| 9,381,144 B1 | 7/2016 | Hilt |
| 9,446,265 B2 | 9/2016 | Jansen |
| 9,468,597 B1 | 10/2016 | Perry |
| 9,474,699 B2 | 10/2016 | Sun |
| 9,486,394 B2 | 11/2016 | Abram |
| 9,526,690 B2 | 12/2016 | Da Costa Pereira |
| 9,655,934 B2 | 5/2017 | Schiemann |
| 9,775,789 B2 | 10/2017 | Simmons |
| 9,795,544 B2 | 10/2017 | Lorant |
| 9,820,482 B2 | 11/2017 | Bingham |
| 9,833,398 B2 | 12/2017 | Hakozaki |
| 9,834,635 B2 | 12/2017 | Klug |
| 9,867,774 B1 | 1/2018 | Hakim |
| 9,895,300 B2 | 2/2018 | Schroeder |
| 9,949,902 B2 | 4/2018 | Mundschau |
| 10,124,030 B2 | 11/2018 | Goldsberry |
| 10,130,578 B2 | 11/2018 | Brillouet |
| 10,363,209 B2 | 7/2019 | Wu |
| 10,398,640 B2 | 9/2019 | Widgerow |
| 10,413,485 B2 | 9/2019 | Huang |
| 10,441,822 B2 | 10/2019 | Buckley |
| 10,449,126 B2 | 10/2019 | L'alloret |
| 10,660,838 B2 | 5/2020 | Hakozaki |
| 2001/0009671 A1 | 7/2001 | Helbiche |
| 2001/0024655 A1 | 9/2001 | Schneider |
| 2002/0022040 A1 | 2/2002 | Robinson |
| 2002/0022052 A1 | 2/2002 | Dransfield |
| 2002/0042438 A1 | 4/2002 | Pelletier |
| 2002/0058704 A1 | 5/2002 | Malik |
| 2002/0168423 A1 | 11/2002 | Wurzburger |
| 2002/0193264 A1 | 12/2002 | Cannell et al. |
| 2003/0032617 A1 | 2/2003 | Harel |
| 2003/0049212 A1 | 3/2003 | Robinson |
| 2003/0091603 A1 | 5/2003 | Ohmori |
| 2003/0118620 A1 | 6/2003 | Zhang |
| 2003/0147968 A1 | 8/2003 | Farber |
| 2003/0158363 A1 | 8/2003 | Nakanishi |
| 2003/0165552 A1 | 9/2003 | Fox |
| 2003/0223982 A1 | 12/2003 | Schlotmann |
| 2004/0013784 A1 | 1/2004 | Costa |
| 2004/0028634 A1 | 2/2004 | Tanaka |
| 2004/0081672 A1 | 4/2004 | Gupta |
| 2004/0092482 A1 | 5/2004 | Gupta |
| 2004/0175347 A1 | 9/2004 | Bissett |
| 2004/0265268 A1 | 12/2004 | Jain |
| 2005/0008601 A1 | 1/2005 | Ariotto |
| 2005/0037036 A1 | 2/2005 | Nielsen |
| 2005/0100519 A1 | 5/2005 | Guth |
| 2005/0106194 A1 | 5/2005 | Schiltz |
| 2005/0170013 A1 | 8/2005 | Douglas |
| 2005/0176677 A1 | 8/2005 | Dal Farra |
| 2005/0227327 A1 | 10/2005 | Brenner |
| 2005/0244348 A1 | 11/2005 | Lindemann |
| 2005/0267023 A1 | 12/2005 | Sinclair |
| 2006/0018861 A1 | 1/2006 | Chen |
| 2006/0034875 A1 | 2/2006 | Nakanishi |
| 2006/0040851 A1 | 2/2006 | Ghosh |
| 2006/0127426 A1 | 6/2006 | Ross |
| 2006/0147508 A1 | 7/2006 | Gupta |
| 2006/0161121 A1 | 7/2006 | Klaveness |
| 2006/0165741 A1 | 7/2006 | Coffindaffer |
| 2006/0210499 A1 | 9/2006 | Hoeffkes |
| 2006/0229265 A1 | 10/2006 | Milburn |
| 2006/0275237 A1 | 12/2006 | Bissett |
| 2007/0003502 A1* | 1/2007 | Tanabe .............. A61Q 7/00 424/70.13 |
| 2007/0027095 A1 | 2/2007 | Brenner |
| 2007/0196344 A1 | 8/2007 | Osborne |
| 2007/0231288 A1 | 10/2007 | Arnaud et al. |
| 2007/0232508 A1 | 10/2007 | Oshimura |
| 2007/0232687 A1 | 10/2007 | Kato |
| 2008/0025932 A1 | 1/2008 | Bissett |
| 2008/0057138 A1 | 3/2008 | Telford |
| 2008/0181956 A1 | 7/2008 | Ha et al. |
| 2008/0206169 A1 | 8/2008 | Millikin |
| 2008/0206373 A1 | 8/2008 | Millikin |
| 2008/0247960 A1 | 10/2008 | Yuan |
| 2008/0287533 A1 | 11/2008 | Gupta |
| 2008/0312169 A1 | 12/2008 | Johnson et al. |

(56) References Cited

U.S. PATENT DOCUMENTS

| | | |
|---|---|---|
| 2008/0317795 A1 | 12/2008 | Traynor |
| 2009/0068219 A1 | 3/2009 | Elie |
| 2009/0196942 A1 | 8/2009 | Goyarts |
| 2009/0197819 A1 | 8/2009 | Johnson et al. |
| 2009/0214628 A1 | 8/2009 | De Rijk |
| 2009/0215723 A1 | 8/2009 | Le |
| 2009/0232750 A1 | 9/2009 | St. Cyr |
| 2009/0317354 A1 | 12/2009 | Nishimura |
| 2010/0015072 A1 | 1/2010 | Polla |
| 2010/0040608 A1 | 2/2010 | Wahren-herlenius |
| 2010/0092408 A1 | 4/2010 | Breyfogle |
| 2010/0092412 A1 | 4/2010 | Gohier |
| 2010/0105638 A1 | 4/2010 | Den-braven |
| 2010/0183531 A1 | 7/2010 | Johncock |
| 2010/0189669 A1 | 7/2010 | Hakozaki |
| 2010/0203175 A1 | 8/2010 | Abdul-malak |
| 2010/0204323 A1 | 8/2010 | Theiler |
| 2010/0215726 A1 | 8/2010 | Roth |
| 2010/0239510 A1 | 9/2010 | Ha |
| 2010/0254919 A1 | 10/2010 | Bommarito |
| 2010/0272667 A1 | 10/2010 | Kyte, III |
| 2010/0291190 A1 | 11/2010 | Giampapa |
| 2011/0097286 A1 | 4/2011 | Swanson |
| 2011/0101021 A1 | 5/2011 | Greer |
| 2011/0117219 A1 | 5/2011 | Springer |
| 2011/0123467 A1 | 5/2011 | Roth |
| 2011/0152384 A1 | 6/2011 | Gunn |
| 2011/0158920 A1 | 6/2011 | Morley |
| 2011/0172160 A1 | 7/2011 | Cao |
| 2011/0229427 A1 | 9/2011 | Klug |
| 2011/0262025 A1 | 10/2011 | Jarrold |
| 2011/0262560 A1 | 10/2011 | Dabe |
| 2012/0003168 A1 | 1/2012 | Lyga |
| 2012/0022013 A1 | 1/2012 | Sinclair |
| 2012/0039967 A1 | 2/2012 | Lou |
| 2012/0093896 A1 | 4/2012 | Mongiat |
| 2012/0121534 A1 | 5/2012 | Thorel |
| 2012/0128683 A1 | 5/2012 | Shantha |
| 2012/0148515 A1 | 6/2012 | Hakozaki |
| 2012/0156146 A1 | 6/2012 | Hakozaki |
| 2012/0172584 A1 | 7/2012 | Sauve |
| 2012/0189684 A1 | 7/2012 | Buckley |
| 2012/0197016 A1 | 8/2012 | Laughlin, II |
| 2012/0225050 A1 | 9/2012 | Knight |
| 2013/0022557 A1 | 1/2013 | Swanson |
| 2013/0125317 A1 | 5/2013 | Rudolph |
| 2013/0164234 A1 | 6/2013 | Gruber |
| 2013/0164265 A1 | 6/2013 | Flavin |
| 2013/0189211 A1 | 7/2013 | Marini |
| 2013/0295024 A1 | 11/2013 | Hammer |
| 2013/0319449 A1 | 12/2013 | Xavier |
| 2014/0020701 A1 | 1/2014 | Galderisi |
| 2014/0065099 A1 | 3/2014 | Alvarez |
| 2014/0090660 A1 | 4/2014 | Xavier |
| 2014/0127332 A1 | 5/2014 | Bitler |
| 2014/0158148 A1 | 6/2014 | Mette |
| 2014/0170195 A1 | 6/2014 | Fassih |
| 2014/0190507 A9 | 7/2014 | Xavier |
| 2014/0328775 A1 | 11/2014 | Laughlin, II |
| 2014/0369943 A1 | 12/2014 | Pilz |
| 2015/0065476 A1 | 3/2015 | Aistrup |
| 2015/0164941 A1 | 6/2015 | Munisekhar |
| 2015/0196464 A1 | 7/2015 | Jansen et al. |
| 2015/0209261 A1 | 7/2015 | Ross |
| 2015/0209272 A1 | 7/2015 | Weisman |
| 2015/0272860 A1 | 10/2015 | Mette |
| 2015/0272865 A1 | 10/2015 | Mette |
| 2015/0359723 A1 | 12/2015 | Kim |
| 2016/0077080 A1 | 3/2016 | Laughlin, II |
| 2016/0089324 A1 | 3/2016 | Nijakowski |
| 2016/0095806 A1 | 4/2016 | Farber |
| 2016/0102179 A1 | 4/2016 | Wagner |
| 2016/0128944 A1 | 5/2016 | Chawrai |
| 2016/0151270 A1 | 6/2016 | Brooks |
| 2016/0199404 A1 | 7/2016 | Blotsky |
| 2016/0235646 A1 | 8/2016 | Shah |
| 2016/0250134 A1 | 9/2016 | Castle |
| 2016/0250241 A1 | 9/2016 | Deren-lewis |
| 2016/0317418 A1 | 11/2016 | Hakazaki |
| 2016/0317419 A1 | 11/2016 | Hakazaki |
| 2016/0317420 A1 | 11/2016 | Hakazaki |
| 2016/0374908 A1 | 12/2016 | Hakozaki |
| 2016/0374918 A1 | 12/2016 | Dihora |
| 2016/0374919 A1 | 12/2016 | Hakozaki |
| 2017/0079408 A1 | 3/2017 | Lee |
| 2017/0121746 A1 | 5/2017 | Velasquez |
| 2017/0165160 A1 | 6/2017 | Schulze Zur Wiesche |
| 2017/0172972 A1 | 6/2017 | Buge |
| 2017/0196795 A1 | 7/2017 | Hakozaki |
| 2017/0266099 A1 | 9/2017 | Kroon |
| 2017/0333321 A1 | 11/2017 | Carnali |
| 2017/0360674 A1 | 12/2017 | Schulze Zur Wiesche |
| 2018/0015013 A1 | 1/2018 | Prendergast |
| 2018/0042840 A1 | 2/2018 | Almiñana Domènech |
| 2018/0104175 A1 | 4/2018 | Liu |
| 2018/0140518 A1 | 5/2018 | Deckner |
| 2018/0177703 A1 | 6/2018 | Perricone |
| 2018/0185283 A1 | 7/2018 | Buge |
| 2018/0271760 A1 | 9/2018 | Baca |
| 2018/0271881 A1 | 9/2018 | Buge |
| 2018/0280297 A1 | 10/2018 | Buge |
| 2018/0280298 A1 | 10/2018 | Buge |
| 2018/0311137 A1 | 11/2018 | Mckiernan |
| 2018/0344624 A1 | 12/2018 | Athwal |
| 2018/0369110 A1 | 12/2018 | Hakozaki |
| 2019/0021961 A1 | 1/2019 | Abels |
| 2019/0076811 A1 | 3/2019 | Lei |
| 2019/0125654 A1 | 5/2019 | Goldsberry |
| 2019/0240141 A1 | 8/2019 | Boland |
| 2019/0328631 A1 | 10/2019 | Lou |
| 2019/0380945 A1 | 12/2019 | Hakozaki |
| 2020/0002377 A1 | 1/2020 | Van Den Nest |
| 2020/0009123 A1 | 1/2020 | Hakozaki |

FOREIGN PATENT DOCUMENTS

| | | |
|---|---|---|
| BR | 102013005446 A2 | 6/2015 |
| CA | 2517765 C | 7/2009 |
| CA | 2217032 C | 12/2009 |
| CH | 711092 A2 | 11/2016 |
| CN | 101182299 A | 5/2008 |
| CN | 100418507 C | 9/2008 |
| CN | 100457074 C | 2/2009 |
| CN | 101048375 B | 12/2012 |
| CN | 103070781 A | 5/2013 |
| CN | 103211717 A | 7/2013 |
| CN | 102670469 B | 10/2013 |
| CN | 103565721 A | 2/2014 |
| CN | 102871863 B | 4/2014 |
| CN | 102716511 B | 5/2014 |
| CN | 104095770 | * 10/2014 |
| CN | 104274340 A | 1/2015 |
| CN | 104688617 A | 6/2015 |
| CN | 104688654 A | 6/2015 |
| CN | 104784084 A | 7/2015 |
| CN | 104812363 A | 7/2015 |
| CN | 104873436 A | 9/2015 |
| CN | 104983630 A | 10/2015 |
| CN | 105168677 A | 12/2015 |
| CN | 104168883 B | 5/2016 |
| CN | 105769747 A | 7/2016 |
| CN | 103987372 B | 8/2016 |
| CN | 105997548 A | 10/2016 |
| CN | 106214607 A | 12/2016 |
| CN | 106456476 A | 2/2017 |
| CN | 106729669 A | 5/2017 |
| CN | 106821849 A | 6/2017 |
| CN | 107137299 A | 9/2017 |
| CN | 107320355 A | 11/2017 |
| CN | 107427429 A | 12/2017 |
| CN | 108078889 A | 5/2018 |
| CN | 104095770 B | 6/2018 |
| CN | 105640870 B | 12/2018 |
| CN | 108938445 A | 12/2018 |

(56) References Cited

FOREIGN PATENT DOCUMENTS

| | | | |
|---|---|---|---|
| CN | 109010216 A | 12/2018 |
| CN | 109106806 A | 1/2019 |
| DE | 1949740 A1 | 7/1970 |
| DE | 2423637 A1 | 11/1975 |
| DE | 3029263 A1 | 3/1981 |
| DE | 10063658 A1 | 7/2002 |
| DE | 10063660 A1 | 7/2002 |
| DE | 10139582 A1 | 2/2003 |
| DE | 20220609 U1 | 12/2003 |
| DE | 60104036 T2 | 8/2004 |
| DE | 69828095 T2 | 1/2005 |
| DE | 102004008440 A1 | 9/2005 |
| DE | 102004035737 A1 | 3/2006 |
| DE | 60030917 T2 | 11/2006 |
| DE | 60032597 T2 | 2/2007 |
| DE | 19712980 B4 | 10/2008 |
| DE | 102007036499 A1 | 2/2009 |
| DE | 102007037432 A1 | 2/2009 |
| DE | 102008010921 A1 | 9/2009 |
| DE | 102010026465 A1 | 5/2011 |
| DE | 102010027180 A1 | 5/2011 |
| DE | 102011084904 A1 | 6/2012 |
| DE | 102011087883 A1 | 8/2012 |
| DE | 102011089357 A1 | 8/2012 |
| DE | 102011089612 A1 | 6/2013 |
| DE | 102013225182 A1 | 4/2014 |
| EP | 0315541 A1 | 5/1989 |
| EP | 0350275 A3 | 6/1991 |
| EP | 0826366 A3 | 4/1998 |
| EP | 0995427 A3 | 5/2000 |
| EP | 1417954 A1 | 5/2004 |
| EP | 1459736 A1 | 9/2004 |
| EP | 1618367 A1 | 1/2006 |
| EP | 1815843 A2 | 8/2007 |
| EP | 1949887 A2 | 7/2008 |
| EP | 1779846 B1 | 10/2010 |
| EP | 1997537 A3 | 2/2012 |
| EP | 2020227 B1 | 8/2012 |
| EP | 2548549 A1 | 1/2013 |
| EP | 2033622 B1 | 3/2013 |
| EP | 1276513 B1 | 11/2013 |
| EP | 2057980 B1 | 4/2014 |
| EP | 1435771 B1 | 7/2015 |
| EP | 1609462 B1 | 7/2015 |
| EP | 3040065 A1 | 7/2016 |
| EP | 2793828 B1 | 8/2016 |
| EP | 3050900 A1 | 8/2016 |
| EP | 1776161 B1 | 10/2016 |
| EP | 1852102 B1 | 10/2016 |
| EP | 1904020 B1 | 10/2016 |
| EP | 2308456 B1 | 10/2016 |
| EP | 1786893 B2 | 11/2016 |
| EP | 1672037 B1 | 12/2016 |
| EP | 1813255 B1 | 11/2017 |
| EP | 1475080 B1 | 4/2018 |
| EP | 2263788 B1 | 7/2018 |
| EP | 3220883 B1 | 7/2018 |
| EP | 2696841 B1 | 10/2018 |
| EP | 3122325 B1 | 10/2018 |
| EP | 2677999 B1 | 12/2018 |
| ES | 2236040 T3 | 7/2005 |
| ES | 2222818 B1 | 3/2007 |
| ES | 2542529 T3 | 8/2015 |
| FR | 1464035 A | 7/1966 |
| FR | 2366841 B1 | 2/1980 |
| FR | 2555443 A1 | 5/1985 |
| FR | 2586693 A1 | 3/1987 |
| FR | 2832062 B1 | 2/2004 |
| FR | 2845596 A1 | 4/2004 |
| FR | 2845284 B1 | 12/2004 |
| FR | 2883170 A1 | 9/2006 |
| FR | 2883171 B1 | 5/2007 |
| FR | 2938188 A1 | 5/2010 |
| FR | 2975295 A1 | 11/2012 |
| FR | 2986429 A1 | 8/2013 |
| FR | 2989891 A1 | 11/2013 |
| GB | 2050829 B | 10/1983 |
| GB | 2270259 A | 3/1994 |
| GB | 2472379 A | 2/2011 |
| JP | H0141602 B2 | 9/1989 |
| JP | H0237206 B2 | 8/1990 |
| JP | H0892061 A | 4/1996 |
| JP | H11137212 A | 5/1999 |
| JP | 2954640 B2 | 9/1999 |
| JP | H11240827 A | 9/1999 |
| JP | 2000072616 A | 3/2000 |
| JP | 2000109421 A | 4/2000 |
| JP | 2000119155 A | 4/2000 |
| JP | 2000212061 A | 8/2000 |
| JP | 2001089316 A | 4/2001 |
| JP | 2001107078 A | 4/2001 |
| JP | 2001261570 A | 9/2001 |
| JP | 2002080335 A | 3/2002 |
| JP | 2002145723 A | 5/2002 |
| JP | 2003095842 A | 4/2003 |
| JP | 2003261437 A | 9/2003 |
| JP | 3519269 B2 | 4/2004 |
| JP | 2004123871 A | 4/2004 |
| JP | 2004137176 A | 5/2004 |
| JP | 2004161655 A | 6/2004 |
| JP | 2004210699 A | 7/2004 |
| JP | 2004210700 A | 7/2004 |
| JP | 2004217616 A | 8/2004 |
| JP | 3615759 B2 | 11/2004 |
| JP | 3643038 B2 | 2/2005 |
| JP | 2005035910 A | 2/2005 |
| JP | 2005041861 A | 2/2005 |
| JP | 2005139139 A | 6/2005 |
| JP | 2005162741 A | 6/2005 |
| JP | 2005232092 A | 9/2005 |
| JP | 2005281133 A | 10/2005 |
| JP | 3739100 B2 | 11/2005 |
| JP | 2005306751 A | 11/2005 |
| JP | 2005320260 A | 11/2005 |
| JP | 3747141 B2 | 12/2005 |
| JP | 2006028133 A | 2/2006 |
| JP | 2006143777 A | 6/2006 |
| JP | 3863675 B2 | 10/2006 |
| JP | 2007106697 A | 4/2007 |
| JP | 2007145716 A | 6/2007 |
| JP | 2007297559 A | 11/2007 |
| JP | 4072296 B2 | 1/2008 |
| JP | 2008143838 A | 6/2008 |
| JP | 2008231010 A | 10/2008 |
| JP | 2009024075 A | 2/2009 |
| JP | 4399332 B2 | 10/2009 |
| JP | 2009269919 A | 11/2009 |
| JP | 4589050 B2 | 9/2010 |
| JP | 2010202595 A | 9/2010 |
| JP | 4759912 B2 | 6/2011 |
| JP | 2011213676 A | 10/2011 |
| JP | 2011236176 A | 11/2011 |
| JP | 4931356 B2 | 2/2012 |
| JP | 2012097030 A | 5/2012 |
| JP | 5203623 B2 | 2/2013 |
| JP | 2013053147 A | 3/2013 |
| JP | 2013103892 A | 5/2013 |
| JP | 2013116884 A | 6/2013 |
| JP | 2013121955 A | 6/2013 |
| JP | 2013173730 A | 9/2013 |
| JP | 2013194030 A | 9/2013 |
| JP | 5427422 B2 | 12/2013 |
| JP | 2014001155 A | 1/2014 |
| JP | 2014062077 A | 1/2014 |
| JP | 2014051670 A | 3/2014 |
| JP | 2014080374 A | 5/2014 |
| JP | 2015500269 A | 1/2015 |
| JP | 2015147752 A | 8/2015 |
| JP | 2015178485 A | 10/2015 |
| JP | 5857104 B2 | 12/2015 |
| JP | 2016003199 A | 1/2016 |
| JP | 2016027037 A | 2/2016 |
| JP | 2016504377 A | 2/2016 |
| JP | 2016044171 A | 4/2016 |

(56) References Cited

FOREIGN PATENT DOCUMENTS

| | | |
|---|---|---|
| JP | 2016069306 A | 5/2016 |
| JP | 2016077836 A | 5/2016 |
| JP | 2016098199 A | 5/2016 |
| JP | 6005663 B2 | 9/2016 |
| JP | 2016183152 A | 10/2016 |
| JP | 2016532654 A | 10/2016 |
| JP | 6017953 B2 | 11/2016 |
| JP | 2016536305 A | 11/2016 |
| JP | 2017501225 A | 1/2017 |
| JP | 6183849 B2 | 8/2017 |
| JP | 6184825 B2 | 8/2017 |
| JP | 2017529368 A | 10/2017 |
| JP | 2017210408 A | 11/2017 |
| JP | 6362243 B2 | 7/2018 |
| JP | 2018168102 A | 11/2018 |
| KR | 20050006622 A | 1/2005 |
| KR | 20070014412 A | 2/2007 |
| KR | 20080082802 A | 9/2008 |
| KR | 20110007751 A | 1/2011 |
| KR | 20120087600 A | 8/2012 |
| KR | 20130088224 A | 8/2013 |
| KR | 20140001686 A | 1/2014 |
| KR | 20140055689 A | 5/2014 |
| KR | 101405615 B1 | 6/2014 |
| KR | 20140093349 A | 7/2014 |
| KR | 20140132243 A | 11/2014 |
| KR | 20150066811 A | 6/2015 |
| KR | 20160002093 A | 1/2016 |
| KR | 20160096548 A | 8/2016 |
| KR | 20160101371 A | 8/2016 |
| KR | 20160108971 A | 9/2016 |
| KR | 20160109869 A | 9/2016 |
| KR | 20180008071 A | 1/2018 |
| KR | 20180020664 A | 2/2018 |
| KR | 20180036232 A | 4/2018 |
| KR | 20180060701 A | 6/2018 |
| KR | 20190001136 A | 1/2019 |
| RU | 2400213 C2 | 9/2010 |
| TW | 201244748 A | 11/2012 |
| WO | 8806888 A1 | 9/1988 |
| WO | 9217159 A3 | 1/1993 |
| WO | 9307856 A1 | 4/1993 |
| WO | 9416710 A1 | 8/1994 |
| WO | 9524179 A1 | 9/1995 |
| WO | 9603970 A1 | 2/1996 |
| WO | 9720540 A1 | 6/1997 |
| WO | 9720542 A1 | 6/1997 |
| WO | 9823256 A1 | 6/1998 |
| WO | 9856343 A1 | 12/1998 |
| WO | 9920229 A1 | 4/1999 |
| WO | 9947141 A1 | 9/1999 |
| WO | 9943296 A3 | 11/1999 |
| WO | 9960995 A1 | 12/1999 |
| WO | 0024921 A1 | 5/2000 |
| WO | 0071093 A1 | 11/2000 |
| WO | 0170187 A1 | 9/2001 |
| WO | 0170188 A1 | 9/2001 |
| WO | 0181635 A1 | 11/2001 |
| WO | 0207685 A2 | 1/2002 |
| WO | 0207700 A2 | 1/2002 |
| WO | 0219984 A3 | 8/2002 |
| WO | 03022234 A1 | 3/2003 |
| WO | 2004024115 A1 | 3/2004 |
| WO | 2005004829 A1 | 1/2005 |
| WO | 2005004833 A1 | 1/2005 |
| WO | 2004100862 A3 | 2/2005 |
| WO | 2005034969 A1 | 4/2005 |
| WO | 2005044214 A1 | 5/2005 |
| WO | 2005049782 A1 | 6/2005 |
| WO | 2006040048 A1 | 4/2006 |
| WO | 2006081071 A1 | 8/2006 |
| WO | 2006127987 A2 | 11/2006 |
| WO | 2007002831 A2 | 1/2007 |
| WO | WO2007101493 A1 | 9/2007 |
| WO | 200800534 A1 | 1/2008 |
| WO | 2008003779 A1 | 1/2008 |
| WO | 2008016298 A1 | 2/2008 |
| WO | 2007067735 A3 | 3/2008 |
| WO | 2009099419 A3 | 5/2010 |
| WO | 2009150408 A3 | 5/2010 |
| WO | 2010051852 A1 | 5/2010 |
| WO | 2010058272 A3 | 7/2010 |
| WO | 2011030123 A2 | 3/2011 |
| WO | 2011033858 A1 | 3/2011 |
| WO | 2011004175 A3 | 4/2011 |
| WO | 2011052224 A1 | 5/2011 |
| WO | WO2011074143 A1 | 6/2011 |
| WO | 2012172199 A1 | 12/2012 |
| WO | 2013010032 A1 | 1/2013 |
| WO | 2013088371 A2 | 6/2013 |
| WO | 2011139492 A3 | 7/2013 |
| WO | 2013124820 A1 | 8/2013 |
| WO | 2011038022 A3 | 9/2013 |
| WO | 2013143776 A2 | 10/2013 |
| WO | 2014090513 A1 | 6/2014 |
| WO | 2014131514 A1 | 9/2014 |
| WO | 2014132060 A1 | 9/2014 |
| WO | 2014190128 A1 | 11/2014 |
| WO | 2015007567 A1 | 1/2015 |
| WO | 2015030702 A2 | 3/2015 |
| WO | 2015061512 A1 | 4/2015 |
| WO | 2015117757 A1 | 8/2015 |
| WO | 2015186114 A1 | 12/2015 |
| WO | 2016006821 A1 | 1/2016 |
| WO | WO2016034519 A1 | 3/2016 |
| WO | 2015174772 A9 | 6/2016 |
| WO | 2016097985 A1 | 6/2016 |
| WO | 2016100634 A2 | 6/2016 |
| WO | WO2016142551 A1 | 9/2016 |
| WO | 2016171464 A1 | 10/2016 |
| WO | WO2016188691 A1 | 12/2016 |
| WO | 2017093788 A1 | 6/2017 |
| WO | WO2017123512 A1 | 7/2017 |
| WO | 2017174756 A1 | 10/2017 |
| WO | 2017191382 A1 | 11/2017 |
| WO | 2017194268 A1 | 11/2017 |
| WO | 2017194292 A1 | 11/2017 |
| WO | 2017200979 A1 | 11/2017 |
| WO | 2018062922 A1 | 4/2018 |
| WO | 2018071640 A1 | 4/2018 |
| WO | 2018112586 A1 | 6/2018 |
| WO | 2018134714 A1 | 7/2018 |
| WO | 2018160509 A1 | 9/2018 |
| WO | 2018189194 A1 | 10/2018 |
| WO | 2018191296 A1 | 10/2018 |
| WO | 2018206962 A1 | 11/2018 |
| WO | 2019245011 A1 | 12/2019 |

OTHER PUBLICATIONS

Eisele et al., The partial compositional characteristics of apple juice from 175 apple varieties, Journal of Food Composition and Analysis, vol. 18, No. 2-3, Mar. 1, 2005, pp. 213-221.

International Search Report and Written Opinion of the International Searching Authority, PCT/US2018/038903, dated Aug. 31, 2018, 16 pages.

Khalifah et al., Kinetics of Nonenzymatic Glycation of Ribonuclease A Leading to Advanced Glycation End Products. Paradoxical Inhibition by Ribose Leads to Facile Isolation of Protein Intermediate for Rapid Post-Amadori Studies, Biochemistry, vol. 35, No. 15, Apr. 16, 1996, pp 4645-4654.

Sinthupoom et al., Nicotinic acid and derivatives as multifunctional pharmacophores for medical applications, European Food Research and Technology, vol. 240, No. 1, Oct. 29, 2014, pp. 1-17.

Trojahn et al., Characterizing Facial Skin Ageing in Humans : Disentangling Extrinsic from Intrinsic Biological Phenomena, BioMed Research International, vol. 2015, Article ID 318586, 9 pages, http://dx.doi.org/10.1155/2015/318586, Jan. 14, 2015.

www.gnpd.com Record ID: 3708793, Anti-Wrinkle Face Cream, Neogen Agecure, Mar. 2016.

(56) References Cited

OTHER PUBLICATIONS

Bissett et al., "Topical niacinamide reduces yellowing, wrinkling, red blotchiness, and hyperpigmented spots in aging facial skin", International Journal of Cosmetic Science, 2004, vol. 26, pp. 231-238.

Draelos et al., "Niacinamide-containing facial moisturizer improves skin barrier and benefits subjects with rosacea", Cutis, vol. 76, Aug. 2005, pp. 135-141.

Ebanks et al., "Mechanisms Regulating Skin Pigmentation: The Rise and Fall of Complexion Coloration", International Journal of Molecular Sciences, vol. 10, No. 9, Sep. 2009, pp. 4066-4087.

Ekman, et al., Overexpression of Psoriasin (S100A7) Contributes to Dysregulated Differentiation in Psoriasis, Acta Derm Venereol, Apr. 6, 2017, 97(4); 441-448.

Ferraz et al., "Kinetic α-Deuterium Isotope Effects for Enzymatic and Nonenzymatic Hydrolysis of Nicotinamide-β-Riboside", Archives of Biochemistry and Biophysics, vol. 191, No. 2, Dec. 1978, pp. 431-436.

Gillbro, et al., The use of gene arrays and corresponding connectivity mapping (Cmap) to identify navel anti-ageing ingredients, International Journal of Cosmetic Science, 2015, 37 (Suppl. 1), 9-14.

Glaser, et al., The Antimicrobial Protein Psoriasin (S100A7) Is Upregulated in Atopic Dermatitis and after Experimental Skin Barrier Disruption, Journal of Investigative Dermatology (2009), 129(3), 641-649; published online Aug. 28, 2008.

Hakozaki et al., "The effect of niacinamide on reducing cutaneous pigmentation and suppression of melanosome transfer", British Journal of Dermatology, vol. 147, No. 1, Jul. 1, 2002, pp. 20-31.

Kimball et al., "Reduction in the appearance of facial hyperpigmentation after use of moisturizers with a combination of topical niacinamide and N-acetyl glucosamine: results of a randomized, double-blind, vehicle-controlled trial", British Journal of Dermatology 2010, vol. 162, No. 2, pp. 435-441.

Oppenheimer, Norman J., "NAD hydrolysis: Chemical and enzymaticmechanisms", Molecular and Cellular Biochemistry, vol. 138, 1994, pp. 245-251.

Seppic, "Sepimax (TM) Zen", Datasheet, 2015. 4 Pages.

Soma et al., "Moisturizing effects of topical nicotinamide on atopic dry skin", International Journal of Dermatology, vol. 44, No. 3, Mar. 2005, pp. 197-202.

Stillman, Alfred E., "Jaundice", Clinical Methods: The History, Physical, and Laboratory Examinations, Edition 3, Chapter 87, Available from: https://www.ncbi.nlm.nih.gov/books/NBK413/, pp. 448-456, (1990).

Superdrug B., "Confident Night Serum", https://www.skincarisma.com/products/b/confident-night-serum/ingredient_list#info-section, 14 pages, (accessed in 2021).

Wohlrab, et al., "Niacinamide—Mechanisms of Action and Its Topical use in Dermatology", Skin Pharmacology and Physiology 2014; vol. 27, pp. 311-315.

www.gnpd.com Record ID: 2347755, "Dark Circle Correcting Eye Swirl", Apr. 2014, 03 pages.

www.gnpd.com Record ID: 3497875, Tria Age-Defying Skincare Nourishing Eye Renewal Cream. Nov. 2015, 05 pages.

Zackheim H.S., Treatment of Psoriasis With 6-Aminonicotinamide. Arch Dermatol. 1975;111(7):880-882. doi:10.1001/archderm.1975.01630190070007.

\* cited by examiner

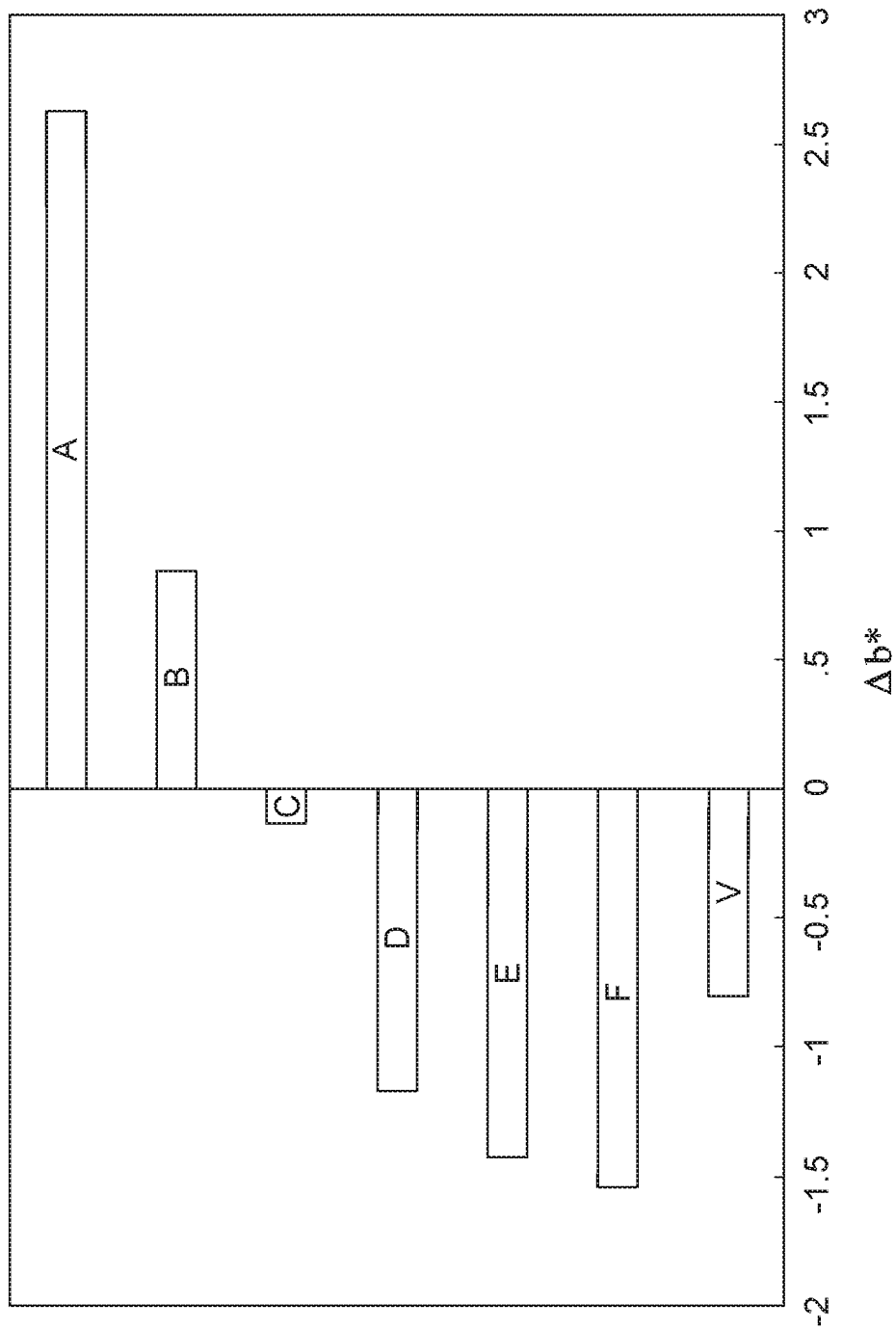

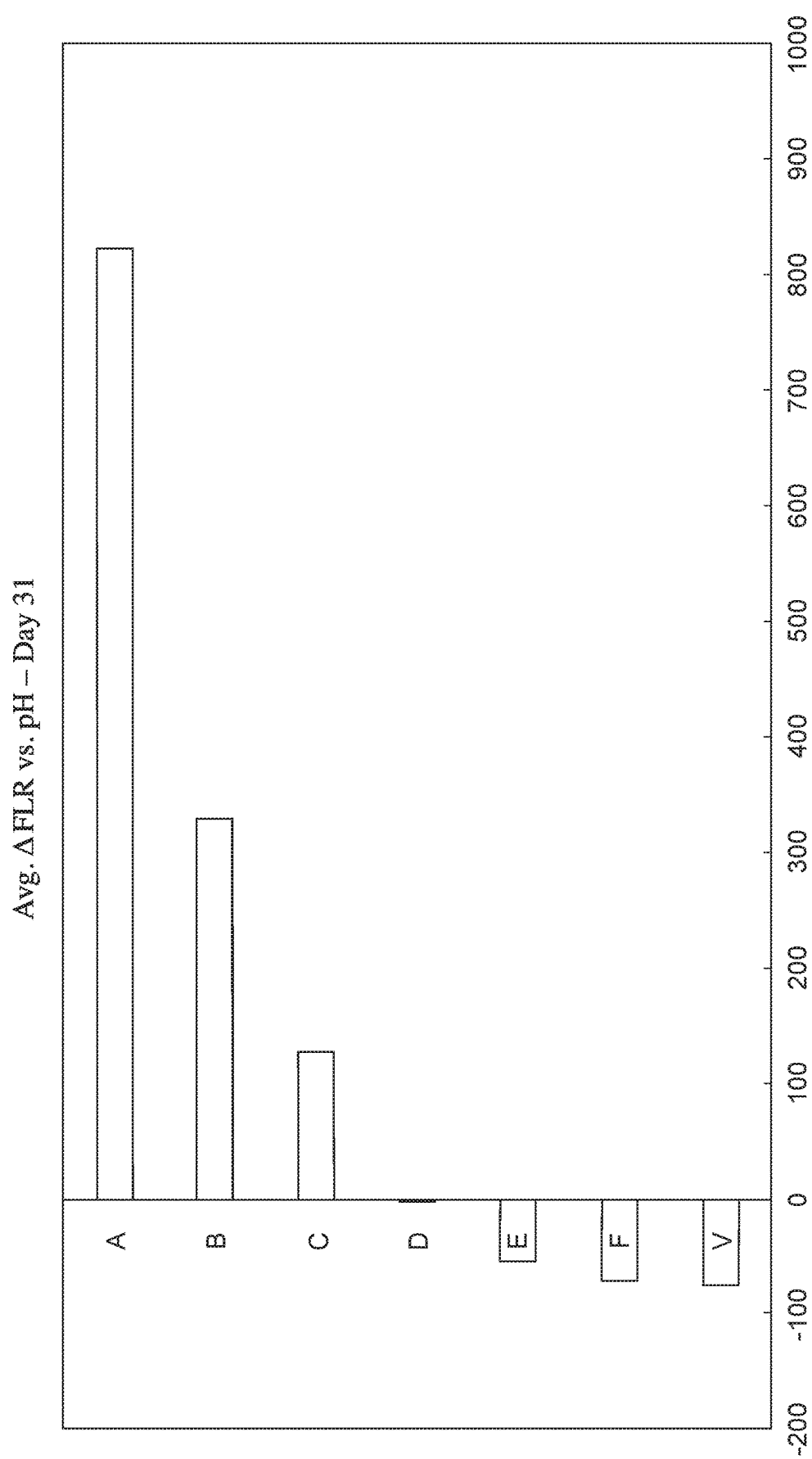

COMPOSITION AND METHOD FOR IMPROVING THE APPEARANCE OF SKIN

FIELD

The present disclosure is directed generally to a cosmetic method of providing a skin health and/or appearance benefit and compositions therefor. More specifically, the present disclosure is directed to methods and compositions that utilize ribose at low pH to provide a skin benefit without causing glycation.

BACKGROUND

Skin is the first line of defense against environmental insults that would otherwise damage sensitive underlying tissue and organs. For example, skin maintains a relatively water-impermeable barrier between an organism and its environment to prevent dehydration. Additionally, skin plays a key role in a person's physical appearance. Generally, most people desire to have younger, healthy looking skin. And to some of these people, the tell-tale signs of skin aging such as thinning skin, wrinkles, and age spots are an undesirable reminder of the disappearance of youth. As a result, treating the signs of aging in skin has become a booming business in youth-conscious societies. Treatments range from cosmetic creams and moisturizers to various forms of cosmetic surgery.

Numerous agents, both natural and synthetic, are known for use in skin care compositions marketed to treat various skin conditions, especially those associated with aging. One example of a well-known skin care agent is ribose. Ribose is a pentose monosaccharide used in the cosmetics industry to provide a variety of skin health benefits. US 2007/0231288 discloses the use of D-ribose in a cosmetic composition to improve the metabolism of skin cells, and thereby improve the function and appearance of the skin. U.S. Pat. No. 6,638,519 describes the use of sugars such as ribose in cosmetic composition as surfactants and moisturizing agents. U.S. Pat. No. 8,911,774 discloses a topical composition for anti-aging skin treatment, which includes D-ribose as "an essential material for the DNA repairing process."

However, sugars such as ribose can also damage skin thru glycation. Glycation is generally recognized as a non-enzymatic process involving a monosaccharide (e.g., glucose or ribose) that reacts with an amino group of an amino acid via a series of reactions characterized by the formation of advance glycation end products ("AGEs"). AGEs can lead to crosslinking of the proteins in skin, especially collagen and elastin, which can manifest as reduced skin elasticity, fine lines and wrinkles, and sallow looking skin. Glycation is also known to increase regularly with age and exposure to ultraviolet radiation.

Accordingly, it would be desirable to provide a cosmetic skin care composition that includes ribose but does not contribute to glycation in skin.

SUMMARY

A topical skin care composition for cosmetically treating a skin condition and/or improving the appearance is described herein. The composition comprises about 0.01% to about 15% of a saccharide incorporated into a dermatologically acceptable carrier. The composition has a pH of less 5.0. The composition is formulated such that the saccharide in the composition does not increase glycation in the collagen matrix of human skin.

Also disclosed is a method of using the low pH compositions of the present invention. The method comprises identifying a target portion of skin where treatment is desired and topically applying the cosmetic composition of the present invention to the target portion of skin during a treatment period. The treatment period should of sufficient length for the composition to improve the condition and/or appearance of the target skin portion.

BRIEF DESCRIPTION OF THE DRAWINGS

FIG. 1. is a chart illustrating the difference in yellowness for ribose-containing compositions at various pH.

FIG. 2 is a chart illustrating the difference in FLR for ribose-containing compositions at various pH.

DETAILED DESCRIPTION

The skin health benefits of saccharides such as ribose are well documented, but may not be suitable for use in some skin care compositions due to their prominent role in glycation. Surprisingly, it has now been discovered that when a saccharide such as ribose is included in a topical skin care composition at a relatively low pH, glycation associated with the saccharide(s) in the collagen matrix of skin can be significantly reduced.

Cosmetic compositions are commonly formulated to have a slightly acidic to slightly basic pH (e.g., pH 5.0 to 8.0) which is believed to improve the stability of certain ingredients in the composition (e.g., niacinamide, salicylates, and neutralized thickeners). However, formulating a skin care composition at a lower pH (e.g., less than pH 5.0, 4.5, 4.0, 3.5, 3.0, or even less than pH 2.5) appears to reduce glycation associated with sugars such as ribose in the collagen matrix of skin. In addition, an acidic skin composition may bolster the acid mantle of the skin, provide flexibility in other types of skin agents that can be included in the composition, and/or provide an exfoliation benefit.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all percentages are by weight of the cosmetic composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods. As used in the description and the appended claims, the singular forms "a," "an," and "the" are intended to include the plural forms as well, unless the context clearly indicates otherwise.

Definitions

"Apply" or "application", as used in reference to a composition, means to apply or spread the compositions of the present invention onto a human skin surface such as the epidermis.

"Cosmetic agent" means any substance, as well any component thereof, intended to be rubbed, poured, sprinkled, sprayed, introduced into, or otherwise applied to a mammalian body or any part thereof to provide a cosmetic effect. Cosmetic agents may include substances that are Generally Recognized as Safe (GRAS) by the US Food and Drug Administration, food additives, and materials used in non-cosmetic consumer products including over-the-counter medications.

"Effective amount" means an amount of a compound or composition sufficient to significantly induce a positive benefit to keratinous tissue over the course of a treatment period. The positive benefit may be a health, appearance, and/or feel benefit, including, independently or in combination, the benefits disclosed herein.

"Hyperpigmented" and "hyperpigmented spot" mean a localized portion of skin with relatively high melanin content. Examples of hyperpigmented spots include, but are not limited to age spots, melasma, chloasma, freckles, post-inflammatory hyperpigmentation, sun-induced pigmented blemishes, and the like.

"Improve the appearance of" means providing a measurable, desirable change or benefit in male and/or female skin appearance, which may be quantified, for example, by a reduction in the Spot Area Fraction of a hyperpigmented spot and/or a decrease in b* value of sallow skin. Exemplary methods for determining improvements in appearance are described in more detail below.

"L*a*b*" refers to the commonly recognized color space specified by the International Commission on Illumination ("CIE"). The three coordinates represent (i) the lightness of the color (i.e., L*=0 yields black and L*=100 indicates diffuse white), (ii) the position of the color between magenta and green (i.e., negative a* values indicate green while positive a* values indicate magenta) and (iii) the position of the color between yellow and blue (i.e., negative b* values indicate blue and positive b* values indicate yellow).

"Low pH," as used herein, refers to cosmetic compositions that have a pH of less than 4.0, but typically greater than 1.0. A suitable method of determining the pH of a composition is described in more detail below.

"Saccharide" means a sugar. Saccharides herein can be mono-, di-, oligo-, or polysaccharides; sugar acids; sugar derivatives; or modified sugars.

"Safe and effective amount" means an effective amount of an ingredient that is low enough to avoid serious side effects (within the scope of sound medical judgment).

"Sallow," when referring to the appearance of skin herein, means an unusual yellow or pale skin tone, with regard to a particular individual, which is commonly associated with an unhealthy state. Sallow-appearing skin can be diagnosed objectively (e.g., with a color value such as L* or b*) or subjectively (e.g., by a skin care professional or consumer).

"Skin care" means regulating and/or improving a skin condition. Some nonlimiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

"Skin care active" means a compound or combination of compounds that, when applied to skin, provide an acute and/or chronic benefit to skin or a type of cell commonly found therein. Skin care actives may regulate and/or improve skin or its associated cells (e.g., improve skin elasticity, hydration, skin barrier function, and/or cell metabolism).

"Skin care composition" means a composition that includes a skin care active and regulates and/or improves skin condition.

"Skin tone" means the overall appearance of basal skin color or color evenness. Skin tone is typically characterized over a larger area of the skin, which is generally more than 100 $mm^2$, up to and including the entirety of the facial skin or other bodily skin surface (e.g., arms, legs, back, hands, neck, chest and abdomen). Skin tone can be measured by image analysis. One measure of skin tone is lightness, which can be measured by the L* coordinate in the L*a*b* color space (International Commission on Illumination). Chromophore mapping such as melanin mapping and melanin concentration may also be used as an indicator of skin tone. Mean melanin may be calculated from the chromophore map data. Additionally, skin tone can be correlated to melanin evenness (e.g., standard deviation) which also may be calculated from the chromophore map data.

"Treatment period," as used herein, means the length of time and/or frequency that a material or composition is applied to a target skin surface.

"Vehicle control" means a negative control that is identical to the test composition except that it does include the particular active(s) of interest (e.g., does not contain ribose).

Cosmetic Compositions

The cosmetic compositions herein are intended for topical application to skin. The present compositions may be used to treat a variety of skin conditions such as, for example, those associated with or caused by inflammation; sun damage; aging (intrinsic or extrinsic); hyperpigmentation (e.g., age spots); seborrheic keratosis; actinic keratosis; UV exposure; skin sallowness or yellowness; skin dullness; skin redness; sebum secretion; rough texture, wrinkles, compromised skin barrier (e.g., dry skin); contact dermatitis; atopic dermatitis; eczema; keratinization disorders; psoriasis; wound healing; and the like.

These cosmetic compositions herein include an effective amount of a suitable saccharide such as ribose (e.g., D-ribose) and a dermatologically acceptable carrier. The present composition may optionally include one or more skin actives of the type commonly included in cosmetic skin care compositions. Non-limiting examples of saccharides that may be suitable for use herein include trioses such as glyceraldehyde and dihydroxyacetone; tetroses such as erythrose, threose, erythrulose; pentoses such as ribose, arabinose, ribulose, xylulose, xylose, lyxose, deoxyribose, dibulose, ribonic acid, and ribaric acid; hexoses such as allose, altrose, glucose, galactose, mannose, fructose, idose, talose, psicose, sorbose, tagatose, gulose, fucose, rhamnose, glucuronic acid, aldose, aldonic acid, glucaric acid, gularic acid, galactaric acid, galacturonic acid; heptoses such as sedoheptulose; nonoses such as neuraminic acid; saccharide derivatives such as ribulose 5-phosphate, xylulose 5-phosphate, ribose 5-phosphate, sedoheptulose 7-phosphate, glyceraldehyde 3-phosphate, fructose 6-phosphate, erythrose 4-phosphate, glucose 6-phosphate, 6-phosphoglucono-5-lactone, 6-phosphogluconate, dihydroxyacetone phosphate, fructose 1,6-bisphosphate; glycosides such as xyloside; xylitol; trehalose; and modified saccharides such as N-acetylglucosamine, N-acetylgalactosamine, and glucosamine. A particularly suitable saccharide for use herein is RIBOXYL brand ribose available from Lucas Meyer Cosmetics, France. The saccharide may be present at between 0.05% and 15% by weight of the composition (e.g., 1%, to 15%, 2% to 10%, 3% to 8% or even 4% to 6%).

The cosmetic compositions herein are formulated to have a relatively low pH (e.g., less than 5.0, 4.5, 4.0, 3.5, 3.0, or even less than 2.5) and may be provided in various product forms that include, but are not limited to, solutions, suspensions, lotions, creams, gels, toners, sticks, sprays, aerosols, ointments, cleansing liquid washes and solid bars, pastes, foams, mousses, shaving creams, wipes, strips, patches, electrically-powered patches, hydrogels, film-forming products, facial and skin masks (with and without insoluble sheet), make-up such as foundations, eye liners, and eye shadows, and the like. The cosmetic composition form may follow from the particular dermatologically acceptable carrier chosen, if present in the composition. The cosmetic compositions herein may be made using conventional methods of making such compositions.

Dermatologically Acceptable Carrier

The compositions herein include a dermatologically acceptable carrier (which may be referred to as a "carrier"). The phrase "dermatologically acceptable carrier" means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. In some instances, the solubility or dispersibility of the components (e.g., extracts, sunscreen active, additional components) may dictate the form and character of the carrier. Non-limiting examples include simple solutions (e.g., aqueous or anhydrous), dispersions, emulsions, and solid forms (e.g., gels, sticks, flowable solids, or amorphous materials). In certain embodiments, the dermatologically acceptable carrier is in the form of an emulsion. Emulsion may be generally classified as having a continuous aqueous phase (e.g., oil-in-water and water-in-oil-in-water) or a continuous oil phase (e.g., water-in-oil or oil-in-water). The oil phase of the present invention may comprise silicone oils, non-silicone oils such as hydrocarbon oils, esters, ethers, and mixtures thereof. The aqueous phase typically comprises water and water-soluble ingredients (e.g., water-soluble moisturizing agents, conditioning agents, anti-microbials, humectants and/or other skin care actives). However, in some instances, the aqueous phase may comprise components other than water, including but not limited to water-soluble moisturizing agents, conditioning agents, anti-microbials, humectants and/or other water-soluble skin care actives. In some instances, the non-water component of the composition comprises a humectant such as glycerin and/or other polyol(s). Emulsions may also contain an emulsifier, e.g., from about 1% to about 10% or from about 2% to about 5% based on the weight of the carrier. Emulsifiers may be nonionic, anionic or cationic. Some suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's Detergents and Emulsifiers, North American Edition, pages 317-324 (1986), each incorporated herein by reference.

The carrier may contain one or more dermatologically acceptable, hydrophilic diluents. As used herein, "diluent" includes materials in which the niacinamide and/or saccharide can be dispersed, dissolved, or otherwise incorporated. Hydrophilic diluents include water, organic hydrophilic diluents such as lower monovalent alcohols (e.g., C1-C4) and low molecular weight glycols and polyols, including propylene glycol, polyethylene glycol (e.g., Molecular Weight 200-600 g/mole), polypropylene glycol (e.g., Molecular Weight 425-2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof.

Thickeners

In some instances, it may be desirable to use thickeners that tolerate a lower range of pH ("stable fatty alcohol thickener"). For example, neutralized thickeners may degrade at lower pH and thus may not impart the desired thickening or feel properties to the composition. On the other hand, fatty alcohol thickeners such as cetyl alcohols and stearyl alcohols are generally stable at low pH (e.g., pH of less than 5.0 or even between a pH of about 2.5 to about 4.0), and thus particularly suited for use in the low pH compositions herein. Accordingly, the present compositions may be free or substantially free of neutralized thickeners and/or may have from 0.1% to 10% (e.g., from about 0.5% to about 8%, from about 1.0% to about 5%, or even from about 2% to about 4%) of a stable fatty alcohol thickener.

Sunscreen Actives

In some instances, it may be desirable to include one or more sunscreen actives in the present composition. The compositions of the subject invention may comprise one or more sunscreen actives (or sunscreen agents) and/or ultraviolet light absorbers. Herein, "sunscreen active" includes both sunscreen agents and physical sunblocks. Sunscreen actives and ultraviolet light absorbers may be organic or inorganic. Examples of suitable sunscreen actives and ultraviolet light absorbers are disclosed in Personal Care Product Council's International Cosmetic Ingredient Dictionary and Handbook, Thirteenth Edition, as "sunscreen agents." Particularly suitable sunscreen actives are 2-ethylhexyl-p-methoxycinnamate (commercially available as PARSOL™ MCX), 4,4'-t-butyl methoxydibenzoyl-methane (commercially available as PARSOL™ 1789), 2-hydroxy-4- methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5-trimethylcyclohexylsalicylate, menthyl anthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, zinc oxide, benzylidene camphor and derivatives thereof, titanium dioxide, and mixtures thereof. The composition may include from about 1% to about 20% or even from about 2% to about 10% by weight of the composition, of the sunscreen active and/or ultraviolet light absorber. Exact amounts will vary depending upon the chosen sunscreen active and/or ultraviolet light absorber and the desired Sun Protection Factor (SPF), and are within the knowledge and judgment of one of skill in the art.

Other Optional Ingredients.

The present composition may optionally include one or more additional ingredients commonly used in cosmetic compositions (e.g., colorants, skin care actives, anti-inflammatory agents, sunscreen agents, emulsifiers, buffers, rheology modifiers, combinations of these and the like), provided that the additional ingredients do not undesirably alter the skin health or appearance benefits provided by the present compositions. The additional ingredients, when incorporated into the composition, should be suitable for use in contact with human skin tissue without undue toxicity, incompatibility, instability, allergic response, and the like. Some nonlimiting examples of additional actives include vitamins, minerals, peptides and peptide derivatives, sugar amines, sunscreens, oil control agents, particulates, flavonoid compounds, hair growth regulators, anti-oxidants and/or anti-oxidant precursors, preservatives, protease inhibitors, tyrosinase inhibitors, anti-inflammatory agents, moisturizing agents, exfoliating agents, skin lightening agents, sunless tanning agents, lubricants, anti-acne actives, anti-cellulite actives, chelating agents, anti-wrinkle actives, anti-atrophy actives, phytosterols and/or plant hormones, N-acyl amino acid compounds, antimicrobials, and antifungals. Other non-limiting examples of additional ingredients and/or skin care actives that may be suitable for use herein are described in U.S. Publication Nos. 2002/0022040; 2003/0049212; 2004/0175347; 2006/0275237; 2007/0196344; 2008/0181956; 2008/0206373; 2010/00092408; 2008/0206373; 2010/0239510; 2010/0189669; 2010/0272667; 2011/0262025; 2011/0097286; 2012/0197016; 2012/0128683; 2012/0148515; 2012/0156146; and 2013/0022557; and U.S. Pat. Nos. 5,939,082; 5,872,112; 6,492,326; 6,696,049; 6,524,598; 5,972,359; and 6,174,533.

When including optional ingredients in the compositions herein, it may be desirable to select ingredients that do not form complexes or otherwise undesirably interact with other ingredients in the composition at low pH, especially pH sensitive ingredients like niacinamide, salicylates and peptides. In some instances, it may be desirable to select skin care actives that function via different biological pathways so that the actives do not interfere with one another, which could reduce the efficacy of both agents. When present, the optional ingredients may be included at amounts of from 0.0001% to 50%; from 0.001% to 20%; or even from 0.01% to 10% (e.g., 50%, 40%, 30%, 20%, 10%, 5%, 4%, 3%, 2%, 1%, 0.5% or 0.1%), by weight of the composition.

Methods of Use

The present method includes identifying a target portion of skin (e.g., a facial skin surface such as the forehead, perioral, chin, periorbital, nose, and/or cheek) in need of treatment and applying a low pH composition comprising a saccharide (e.g., ribose), and optionally one or more additional skin care agents, to the target portion of skin. In some instances, the target portion of skin may have a sallow skin tone or exhibit some other undesirable skin condition. In some instances, the target portion of skin may not appear to be suffering from a skin condition such as one associated with the effects of glycation, but a user (e.g., a relatively young user) may still wish to target such an area of skin if it is one that typically exhibits the undesirable effects of glycation or some other skin condition later in life (e.g., skin surfaces that are typically not covered by clothing, such as facial skin surfaces, hand and arm skin surfaces, foot and leg skin surfaces, and neck and chest skin surfaces). In this way, the present compositions may be used in a preventative capacity. The composition may be applied to the target skin portion and, if desired, to the surrounding skin at least once a day, twice a day, or on a more frequent daily basis, during a treatment period. When applied twice daily, the first and second applications are separated by at least 1 to 12 hours. Typically, the composition is applied in the morning and/or in the evening before bed. When used according to the methods herein, the present composition may improve the appearance of a skin condition without causing glycation.

The treatment period is ideally of sufficient time for a skin active present in the low pH composition to improve the appearance of a target portion of skin. In some instances, the saccharide-containing, low pH compositions herein may even reduce glycation, for example, when compared to a vehicle control. The treatment period may last for at least 1 week (e.g., about 2 weeks, 4 weeks, 8 weeks, or even 12 weeks). In some instances, the treatment period will extend over multiple months (i.e., 3-12 months) or multiple years. In some instances, the composition may be applied most days of the week (e.g., at least 4, 5 or 6 days a week), at least once a day or even twice a day during a treatment period of at least 2 weeks, 4 weeks, 8 weeks, or 12 weeks.

The step of applying the composition may be accomplished by localized application. In reference to application of the composition, the terms "localized", "local", or "locally" mean that the composition is delivered to the targeted area (e.g., a hyperpigmented spot or portion thereof) while minimizing delivery to skin surfaces where treatment is not desired. The composition may be applied and lightly massaged into an area of skin. The form of the composition or the dermatologically acceptable carrier should be selected to facilitate localized application. While certain embodiments herein contemplate applying a composition locally to an area, it will be appreciated that compositions herein can be applied more generally or broadly to one or more skin surfaces. In certain embodiments, the compositions herein may be used as part of a multi-step beauty regimen, wherein the present composition may be applied before and/or after one or more other compositions.

Advanced Glycation End Product Assay

The AGE assay provides an in vitro method of determining how a test agent impacts glycation. In particular, a saccharide can be applied to gelatin, which acts as a surrogate for collagen (i.e., a heterogeneous mixture of high-average-molecular-mass, water-soluble proteins present in collagen), at a particular pH and the resulting AGEs detected by a spectrophotometer. When a saccharide such as ribose is added to the sample, it reacts with the proteins in the gelatin, much in the same way as it would with collagen, to produce AGEs. The spectrophotometer detects the fluorescence intensity ("FLR") or yellowness (b*) associated with the resulting AGEs, which can then be correlated to the amount of glycation that occurs in skin. Lower b* and FLR values correspond to less AGEs, and thus less glycation.

Three replicates of each test samples are prepared in a 96-well plate (e.g., a FALCON brand 96-well tissue culture plate or equivalent) at a total volume of 250 µl/well. The plate(s) containing the test samples are placed in a standard cell culture incubator (e.g., THERMO SCIENTIFIC FORMA brand incubator available from Fisher Scientific, Waltham, Mass. or equivalent) and incubated for the duration of the test at 37° C. with 5% $CO_2$ and 95% relative humidity. Fluorescence intensity and yellowness are measured at the start of test (time=0) and generally monitored on a daily basis except for weekends. To measure FLR or b*, the plate(s) containing the test samples are removed from the incubator and placed in a SPECTRAMAX Plus brand spectrophotometer (available from Molecular Devices, Sunnyvale, Calif.) or equivalent. To detect fluorescence intensity ("FLR"), the spectrophotometer is set at 400/465 nm (ex/em). To detect yellowness (b*), the spectrophotometer is set to collect absorbance spectrum from 350 nm to 750 nm in 10 nm increments. The absorbance spectra from the yellowness measurement are then converted to L*a*b* values by a computer using suitable conversion software.

The change in fluorescence intensity ("ΔFLR") is determined by comparing the FLR of a well at a sampling time point to the initial FLR at time=0. The change in yellowness ("Δb*") at a particular time point is determined by comparing the initial b* value at time=0 to the b* value at the time point of interest.

EXAMPLE

The effect of pH on glycation was determined for a ribose-containing composition across a range of pH (i.e., pH 6.8, 5, 4.5, 4, 3.5, and 2.5). The test samples were prepared in triplicate of 1-ml volume for each testing leg to accommodate threshold volume needed for small volume pH titration process. Each 1-ml volume of sample is made using a combination of 450 ul of 2% w/v gelatin solution (available from Sigma as Catalog # G1393), 100 ul of 25.9% w/v ribose solution (available from Sigma, Catalog # R7500-25G), and a sufficient quantity of Dulbecco's phosphate buffered saline ("DPBS") (available from Gibco's) to bring the sample volume to 1 ml. IN HCl was used to adjust the pH of the sample to the desired level. After the 1-ml batches are made in triplicate for each treatment leg, 250 ul from each batch is delivered to each well onto a 96-well plate. Each well should contain 112.5 ul of 2% gelatin, 10 ul of 25.9% w/v Ribose solution, and 127.5 ul of DPBS/IN HCl, for a ribose concentration of 2.59% w/v. The vehicle control contained 112.5 µl gelatin and 137.5 µl DPBS and had an unadjusted pH of 6.7.

The average ΔFLR and Δb* in this example were determined for each test sample according to the AGE Assay described above. The duration of the test was 38 days. The pH for each test sample is shown in Table 1. Composition A was used as a positive control and Composition V is the vehicle control. The results of the test are summarized in Tables 2 to 7 below. The results at day 31 are illustrated in FIGS. 1 and 2.

TABLE 1

| Composition | pH |
|---|---|
| A (pos. control) | 6.8 |
| B | 5 |
| C | 4.5 |
| D | 4.0 |
| E | 3.5 |
| F | 2.5 |
| V (neg. control) | 6.7 |

TABLE 2

| Composition | ΔFLR at 20 days | p-value vs. A | p-value vs. V |
|---|---|---|---|
| A | 462 | 1.000 | 0.000 |
| B | 103 | 0.000 | 0.000 |
| C | −3 | 0.000 | 0.000 |
| D | −56 | 0.000 | 0.231 |
| E | −63 | 0.000 | 0.954 |
| F | −68 | 0.000 | 0.297 |
| V | −62 | 0.000 | 1.000 |

TABLE 3

| Composition | Δb* at 20 days | p-value vs. A | p-value vs. V |
|---|---|---|---|
| A | 0.868 | 1.000 | 0.000 |
| B | −0.334 | 0.000 | 0.017 |
| C | −1.026 | 0.000 | 0.386 |
| D | −1.510 | 0.000 | 0.010 |
| E | −1.502 | 0.000 | 0.011 |
| F | −1.409 | 0.000 | 0.019 |
| V | −0.897 | 0.000 | 1.000 |

TABLE 4

| Composition | ΔFLR at 31 days | p-value vs. A | p-value vs. V |
|---|---|---|---|
| A | 822 | 1.000 | 0.000 |
| B | 329 | 0.000 | 0.000 |
| C | 127 | 0.000 | 0.000 |
| D | −2 | 0.000 | 0.000 |
| E | −55 | 0.000 | 0.022 |
| F | −71 | 0.000 | 0.426 |
| V | −75 | 0.000 | 1.000 |

TABLE 5

| Composition | Δb* at 31 days | p-value vs. A | p-value vs. V |
|---|---|---|---|
| A | 2.625 | 1.000 | 0.000 |
| B | 0.845 | 0.000 | 0.001 |
| C | −0.135 | 0.000 | 0.017 |
| D | −1.173 | 0.000 | 0.084 |
| E | −1.426 | 0.000 | 0.016 |
| F | −1.540 | 0.000 | 0.007 |
| V | −0.799 | 0.000 | 1.000 |

TABLE 6

| Composition | ΔFLR at 38 days | p-value vs. A | p-value vs. V |
|---|---|---|---|
| A | 964 | 1.000 | 0.000 |
| B | 463 | 0.000 | 0.000 |
| C | 214 | 0.000 | 0.000 |
| D | 39 | 0.000 | 0.000 |
| E | −50 | 0.000 | 0.004 |
| F | −79 | 0.000 | 0.103 |
| V | −91 | 0.000 | 1.000 |

TABLE 7

| Composition | Δb* at 38 days | p-value vs. A | p-value vs. V |
|---|---|---|---|
| A | 3.771 | 1.000 | 0.000 |
| B | 1.728 | 0.000 | 0.000 |
| C | 0.504 | 0.000 | 0.000 |
| D | −0.811 | 0.000 | 0.239 |
| E | −1.338 | 0.000 | 0.126 |
| F | −1.560 | 0.000 | 0.015 |
| V | −1.033 | 0.000 | 1.000 |

Composition A, which acted as the positive control, showed a continual increase in FLR and yellowness over time as expected. Composition B showed an increase FLR at day 20, 31, and 38, but only showed an increase in yellowness at days 31 and 38. But even at day 20, the decrease in yellowness for composition B significantly improved relative to the negative control (i.e., composition V). Compositions C, D, E, and F exhibited a trend of decreasing fluorescence and yellowness corresponding to the decrease in pH. Surprisingly, compositions D, E, and F even showed an improvement (i.e., decrease) in b* relative to the vehicle control, which suggests that saccharides such as ribose may actually be useful in combatting certain aspects of glycation at lower pH. Thus, it is important to formulate skin care composition that include saccharides such as ribose at lower pH to avoid or even combat the undesirable effects of glycation. Accordingly, the present compositions may reduce the presence of AGEs and/or yellowness in skin when used according to the methods described.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A topical skin care composition, comprising:
   (a) about 0.01% to about 15%, by weight, of a saccharide; and
   (b) a dermatologically acceptable carrier, wherein the composition has a pH of equal to or less than 3.5 and the composition does not increase glycation over time in the Advanced Glycation End Product Assay.

2. The composition of claim 1, wherein the saccharide is selected from the group consisting of glyceraldehyde, dihydroxyacetone, erythrose, threose, erythrulose, ribose, arabinose, ribulose, xylulose, xylose, lyxose, deoxyribose, dibulose, ribonic acid, ribaric acid, allose, altrose, glucose, galactose, mannose, fructose, idose, talose, psicose, trehalose, sorbose, tagatose, gulose, fucose, rhamnose, glucuronic acid, glucaric acid, gularic acid, galactaric acid, galacturonic acid, sedoheptulose, neuraminic acid, ribulose 5-phosphate, xylulose 5-phosphate, ribose 5-phosphate, sedoheptulose 7-phosphate, glyceraldehyde 3-phosphate, fructose 6-phosphate, erythrose 4-phosphate, glucose 6-phosphate, 6-phosphoglucono-δ-lactone, 6-phosphogluconate, dihydroxyacetone phosphate, fructose 1,6-bisphosphate, N-acetylglucosamine, N-acetylgalactosamine, glucosamine, and combinations thereof.

3. The composition of claim 2, wherein the saccharide is ribose or trehalose.

4. The composition of claim 1, further comprising about 0.1% to about 10%, by weight, of a stable fatty alcohol thickener selected from the group consisting of a cetyl alcohol, a stearyl alcohol, and combinations thereof.

5. The composition of claim 4, wherein the stable fatty alcohol thickener is present at about 1% to about 5%, by weight.

6. The composition of claim 1, further comprising an additional skin care active selected from the group consisting of sunscreens, oil control agents, anti-inflammatory agents, moisturizing agents, exfoliating agents, skin lightening agents, anti-acne agents, anti-wrinkle agents, antimicrobials, antifungals, and combinations of distinct agents thereof.

7. The composition of claim 6, wherein the additional skin care active comprises about 0.01% to about 15%, by weight, niacinamide.

8. The composition of claim 6, wherein the addition skin care active is a sunscreen selected from the group consisting of 2-ethylhexyl-p-methoxycinnamate, 4,4'-t-butyl methoxydibenzoyl-methane, 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, trimethylcyclohexylsalicylate, menthyl anthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, zinc oxide, benzylidene camphor, titanium dioxide, and combinations thereof.

9. The composition of claim 6, wherein the additional skin active is selected from the group consisting of sucrose dilaurate, N-acyl phenylanine, hexamidine, hexyldecanol, N-acetyl glucosamine, a combination of 1,2 hexandiol and 1,2 octandiol, hyaluronic acid, sodium hyaluronate, lactic acid, lactate salts, hydroxycinnamic acid, hexylresorcinol, glycyrrhizic acid, bisabolol, and combinations thereof.

10. The composition of claim 1, wherein the composition does not increase a yellowness (b*) value over time in the AGE assay.

11. The composition of claim 1, wherein the composition does not increase a fluorescence intensity value over time in the AGE Assay.

12. The composition of claim 1, further comprising an emulsifier.

13. A topical skin care composition, comprising:
    (a) about 0.01% to about 15%, by weight, of trehalose;
    (b) glycerin;
    (c) a third agent as thickener; and
    (d) a fourth agent as dermatologically acceptable carrier, wherein the composition has a pH of equal to or less than 3.5 and the composition does not increase in the Advanced Glycation End Product Assay.

14. The skin care composition of claim 13, wherein the dermatologically acceptable carrier is in the form of an oil-in-water emulsion.

15. The skin care composition of claim 14, wherein an oil phase of the oil-in-water emulsion comprises a silicone oil.

16. The skin care composition of claim 13, wherein the composition exhibits a change in fluorescence intensity (ΔFLR) of less than 0 relative to an initial FLR at time 0 in the Advanced Glycation End Product Assay after 38 days.

* * * * *